United States Patent
Hsiao

(10) Patent No.: US 9,844,609 B2
(45) Date of Patent: Dec. 19, 2017

(54) AROMA DIFFUSER USING AN AROMA CAPSULE

(71) Applicant: Ming Jen Hsiao, Miaoli County (TW)

(72) Inventor: Ming Jen Hsiao, Miaoli County (TW)

( * ) Notice: Subject to any disclaimer, the term of this patent is extended or adjusted under 35 U.S.C. 154(b) by 0 days.

(21) Appl. No.: 15/258,689

(22) Filed: Sep. 7, 2016

(65) Prior Publication Data
US 2016/0375168 A1 Dec. 29, 2016

Related U.S. Application Data

(63) Continuation-in-part of application No. 14/042,162, filed on Sep. 30, 2013, now Pat. No. 9,498,553, and a continuation-in-part of application No. 14/157,302, filed on Jan. 16, 2014, now Pat. No. 9,500,358, said application No. 14/042,162 is a continuation-in-part of application No. 13/658,820, filed on Oct. 24, 2012, now abandoned, and a continuation-in-part of application No. 13/549,490, filed on Jul. 15, 2012, now Pat. No. 8,668,885, and a continuation-in-part of application No. 13/549,493, filed on Jul. 15, 2012, now abandoned, said application No. 14/157,302 is a continuation-in-part of application No. 13/670,430, filed on Nov. 6, 2012, now Pat. No. 8,938,159, and a continuation-in-part of application No. 13/669,354, filed on Nov. 5, 2012, now Pat. No. 9,109,780, and a continuation-in-part of application No. 13/658,820, filed on Oct. 24, 2012, now abandoned.

(51) Int. Cl.
F22B 29/06 (2006.01)
B01D 3/06 (2006.01)
A61L 9/03 (2006.01)

(52) U.S. Cl.
CPC .......... *A61L 9/03* (2013.01); *A61L 2209/133* (2013.01)

(58) Field of Classification Search
None
See application file for complete search history.

(56) References Cited

U.S. PATENT DOCUMENTS 6,106,786 A * 8/2000 Akahoshi ............... A61L 9/122
  222/187
7,572,412 B2 * 8/2009 Yang ...................... A61L 9/122
  392/386
8,192,041 B2   6/2012 Hsiao
(Continued)

FOREIGN PATENT DOCUMENTS

EP   2679249 A1   1/2014

*Primary Examiner* — Thor Campbell
(74) *Attorney, Agent, or Firm* — Chun-Ming Shih

(57) ABSTRACT

An aroma diffuser using an aroma capsule is disclosed to include a hollow housing including a first opening on a top side thereof, a second opening on a bottom side thereof and an integrated holder member downwardly inwardly extended from a top side thereof and defining therein a holding chamber facing toward the first opening, a heat conduction device mounted in the holding chamber, and a heating element mounted at a bottom side of the heat conduction device and kept in contact with the heat conduction device. Thus, an aroma capsule can be placed in the holding chamber and heated by the heating element to release fragrant vapor. After the aroma contained in the aroma capsule is used up, the aroma capsule can be replaced conveniently and rapidly.

11 Claims, 6 Drawing Sheets

(56) References Cited

U.S. PATENT DOCUMENTS

| | | |
|---|---|---|
| 8,201,957 B2 | 6/2012 | Hsiao |
| 8,668,885 B2 | 3/2014 | Wirz |
| 8,765,073 B1 | 7/2014 | Hsiao |
| 8,772,675 B2 * | 7/2014 | Juarez ..................... H05B 3/26 219/209 |
| 8,787,739 B2 | 7/2014 | Hsiao |
| 8,878,102 B2 * | 11/2014 | Juarez .................... H01R 33/22 219/209 |
| 8,983,277 B2 | 3/2015 | Hsiao |
| 9,028,759 B2 | 5/2015 | Wirz |
| 9,031,392 B2 | 5/2015 | Hsiao |
| 9,211,355 B2 * | 12/2015 | Thompson ................ A61L 9/03 |
| 9,410,695 B2 | 8/2016 | Hsiao |
| 2005/0016985 A1 * | 1/2005 | Haas ......................... A61L 9/03 219/438 |
| 2005/0184045 A1 * | 8/2005 | Shimizu .................... A61L 9/03 219/474 |
| 2008/0279731 A1 * | 11/2008 | Goreham ................ A61L 9/037 422/125 |
| 2010/0096376 A1 * | 4/2010 | Hsiao ........................ A61L 9/03 219/201 |
| 2010/0260646 A1 * | 10/2010 | Jorgensen ............... A61L 9/035 422/125 |
| 2011/0110824 A1 * | 5/2011 | Hsiao ...................... A61L 9/035 422/125 |
| 2014/0110389 A1 | 4/2014 | Hsiao |
| 2015/0109823 A1 | 4/2015 | Hsiao |
| 2015/0117056 A1 | 4/2015 | Hsiao |

* cited by examiner

AROMA DIFFUSER USING AN AROMA CAPSULE

CROSS-REFERENCES TO RELATED APPLICATION

The present invention is a continuation-in-part of patent application Ser. No. 14/042,162 filed on Sep. 30, 2013 and Ser. No. 14/157,302 filed on Jan. 16, 2014.

BACKGROUND OF THE INVENTION

1. Field of the Invention

This invention relates to an aroma diffuser technology and more particularly, to an aroma diffuser using an aroma capsule.

2. Description of Related Art

U.S. Pat. Nos. 8,066,420, 8,262,277 and 8,147,116 disclose an aroma diffuser, which includes a power supply, a heating source, essential oil or aroma wax, and a container for the aroma wax to be contained therein. The essential oil is likely to be leaked from the container as the container is toppled over. After the aroma wax contained in the container is evaporated completely and before a new aroma wax is placed in the container, the user needs to take aroma wax residues out from the container and then to clean the container. During the cleaning process, the user is likely to be stained by the aroma wax residues.

Further, in U.S. patent application Ser. No. 14/157,302, which was invented and filed by the present inventor, the holder member is a separated member. An external assembly step is necessary to install the holder member, increasing the cost. Further, the holder member is not orthopedically designed for finger installation. It is not convenient for the user to place the aroma capsule in the narrow inside space of the heat conduction container in the aroma diffuser with the fingers, or to take the used aroma capsule out of the aroma diffuser. This disadvantage affects the convenience and efficiency of the use of the aroma capsule in the aroma diffuser.

SUMMARY OF THE INVENTION

In view of the problems of the prior art, the present invention provides an aroma diffuser using an aroma capsule. The aroma diffuser can be simply and smoothly combined with a disposable aroma capsule. Since the aroma capsule is disposable, a new aroma capsule can replace the used aroma capsule easily.

Thus, the present invention provides an aroma diffuser using an aroma capsule, which reduces the assembly cost and errors.

In one embodiment of the present invention, the aroma diffuser using an aroma capsule comprises a hollow housing, a heat conduction device and a heating element. The hollow housing comprises a first opening, a second opening and a holder member. The first opening is located on a top side of the hollow housing. The second opening is located on an opposing bottom side of the hollow housing. The holder member is mounted in the hollow housing, defining therein a holding chamber that faces toward the first opening. The heat conduction device is mounted in the holding chamber and abutted to the bottom hole. The heating element is mounted at a bottom side of the heat conduction device, and kept in contact with the heat conduction device. Thus, the heating element is electrically connected to a power supply unit for generating heat to heat the heat conduction device.

When using the aroma diffuser using an aroma capsule, the user can place an aroma capsule in the holding chamber of the holder member through the free end of the heat conduction device, and use a power supply unit to provide electricity to the heating element for generating heat to heat the heat conduction device so that the generated heat energy can be transferred through the heat conduction device to the aroma capsule, causing the aroma capsule to release a fragrant vapor toward the outside of the aroma diffuser.

Unlike the prior art design in which the hollow housing and the holder member are made from different materials and separately mounted, the invention has the hollow housing and the holder member integrally made in one piece without any labor-consuming assembly steps, and thus, the invention saves the component cost of the holder member and enhances the structural stability. During the operation of the heating element to heat the aroma capsule, the heat energy in the holder member and the hollow housing is prohibited from being transferred to the printed circuit board and other electronic components, avoiding thermal damage to the electronic components.

In one embodiment of the present invention, the holder member further comprises an upper arched wall and a lower upright wall surrounding the holding chamber. The upper arched wall curves inwardly from the top side of the hollow housing. Further, the upper arched wall has a wide top and a narrow bottom. The lower upright wall is extended downwardly from the upper arched wall to the inside of the holder member.

The aroma diffuser further comprises an aroma capsule placed in the holding chamber of the holder member. The aroma capsule has a bottom side thereof supported on the lower upright wall and kept in contact with the heat conduction device, and an opposing top side thereof suspended in the upper arched wall and defining with the upper arched wall an arched gap therebetween. After the contained aroma in the aroma capsule is used up, the user can insert his or her plump fingers through the arched gap to pick up the used aroma capsule from the holding chamber of the holder member for replacement, and then place a new aroma capsule in the holding chamber inside the holder member of the aroma diffuser quickly. When compared to the prior art design in which the holder member and an attached external member, the holder member and the hollow housing in accordance with the present invention are integrally made in one piece, and thus, the invention greatly the assembly cost and errors. The design of the invention allows the user to replace the aroma capsule conveniently and efficiently.

BRIEF DESCRIPTION OF DRAWINGS

The invention can be more fully understood by reading the following detailed description of the preferred embodiments, with reference made to the accompanying drawings, wherein.

DETAILED DESCRIPTION OF THE INVENTION

Figure 1:
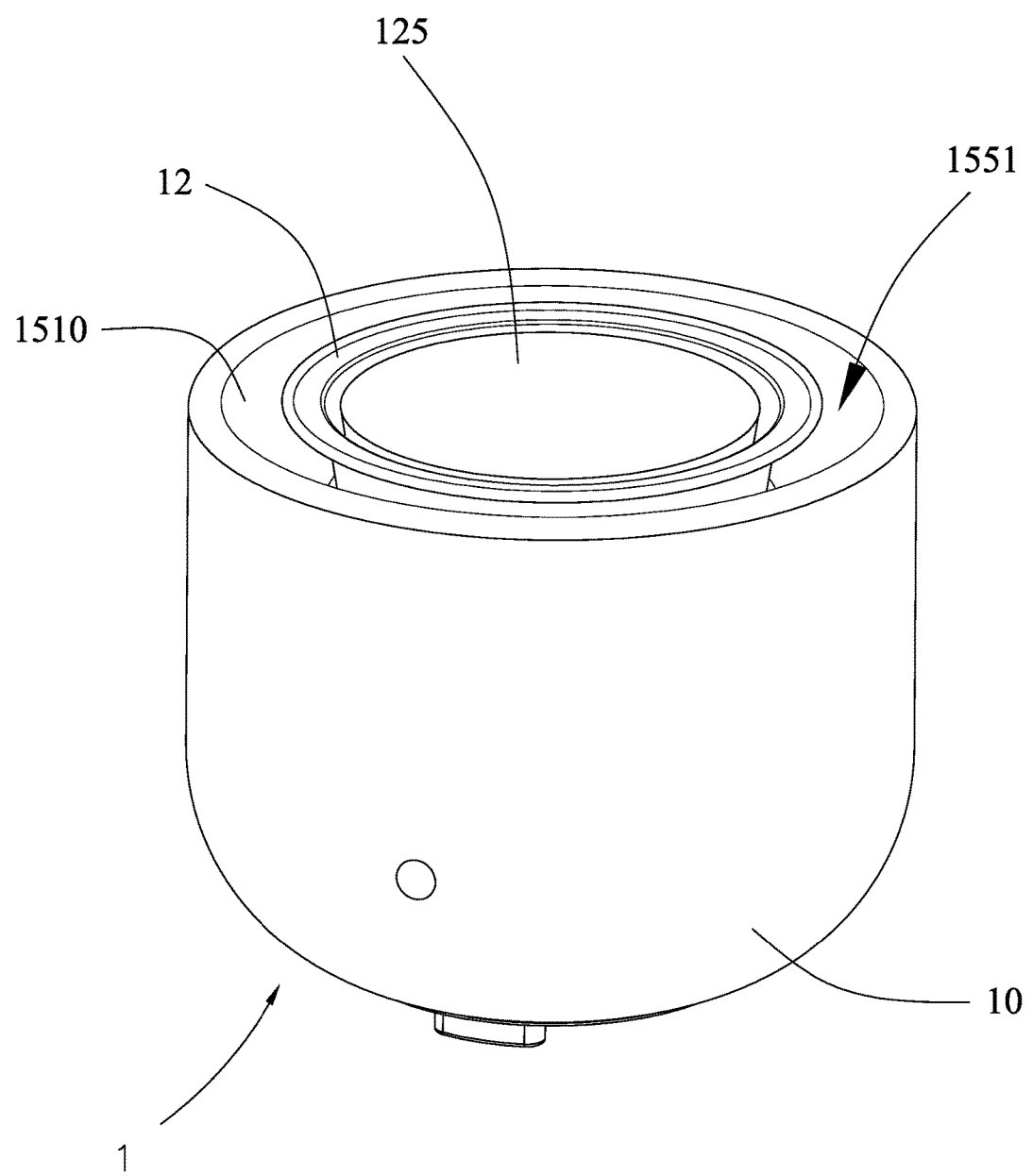
FIG. 1 is an oblique top elevational view of an aroma diffuser having an aroma capsule in accordance with the present invention.
Figure 2:
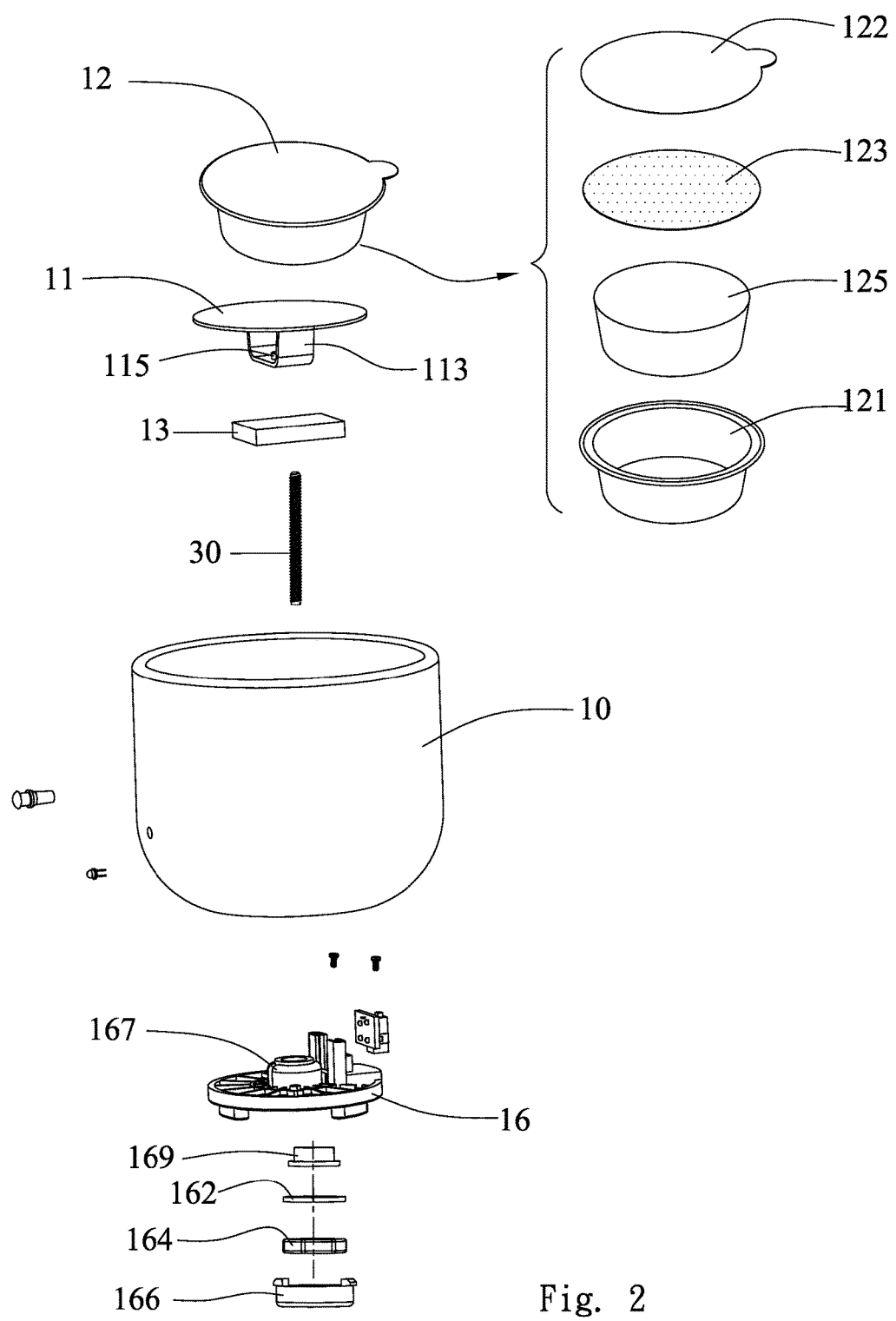
FIG. 2 is an exploded view of the aroma diffuser having an aroma capsule in accordance with the present invention.

The following illustrative embodiments are provided to illustrate the disclosure of the present invention, these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

Refer to FIGS. 1-4. In an embodiment according to the present invention, an aroma diffuser 1 having an aroma capsule comprises a hollow housing 10, a heat conduction device 11, and a heating element 13. The hollow housing 1 comprises a first opening 101, a second opening 103 and a holder member 15. The first opening 101 is defined in a top side of the hollow housing 10. The second opening 103 is defined in an opposing bottom side of the hollow housing 10. The holder member 15 is integrally extended from the top side of the hollow housing 10 toward the inside thereof, defining therein a holding chamber 155 that faces toward the first opening 101. The heat conduction device 11 is mounted in the holding chamber 155 of the holder member 15. The heating element 13 is disposed on a bottom side of the heat conduction device 11 and kept in contact with the heat conduction device 11. The heating element 13 is connectable to a power supply unit (now shown) for generating heat energy to heat the heat conduction device 11 of the aroma diffuser 1.

In this embodiment, an electrical wire (not shown) is inserted through a bottom hole 153 of the holder member 15 to electrically connect the heating element 13 to the power supply unit.

Thus, when using the aroma diffuser 1, the user can put an aroma substance unit through the first opening 101 into the holding chamber 155 of the holder member 15 to keep the aroma substance unit in direct contact with the heat conduction device 11. The power supply unit provides the necessary working power to the heating element 13, causing the heating element 13 to generate heat for heating the heat conduction device 11, enabling the heat energy thus produced to be transferred through the heat conduction device 11 to the aroma substance unit. In this embodiment, the aroma substance unit is an aroma capsule 12. Thus, the aroma capsule 12 is heated to generate fragrance that is diffused upward through the free end 111 of the heat conduction device 11.

Figure 3:
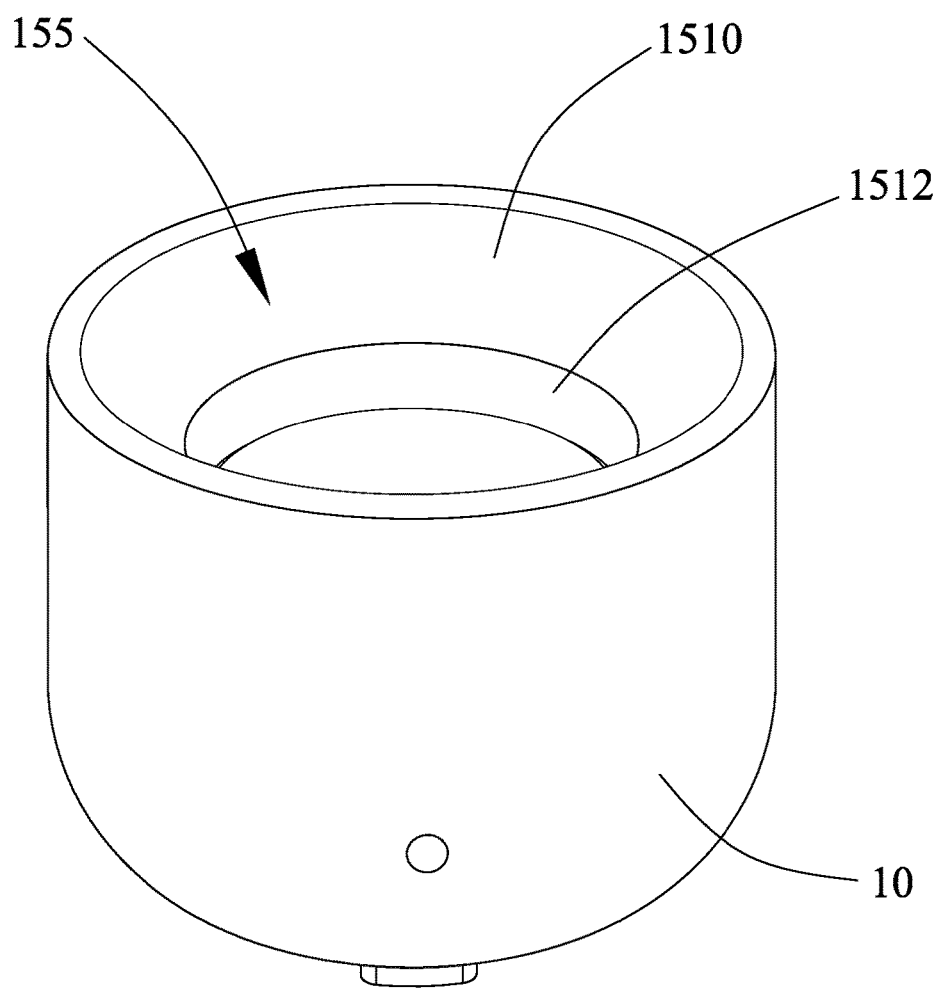
FIG. 3 is an oblique top elevational view of the hollow housing of the aroma diffuser having an aroma capsule in accordance with the present invention.
Figure 4:
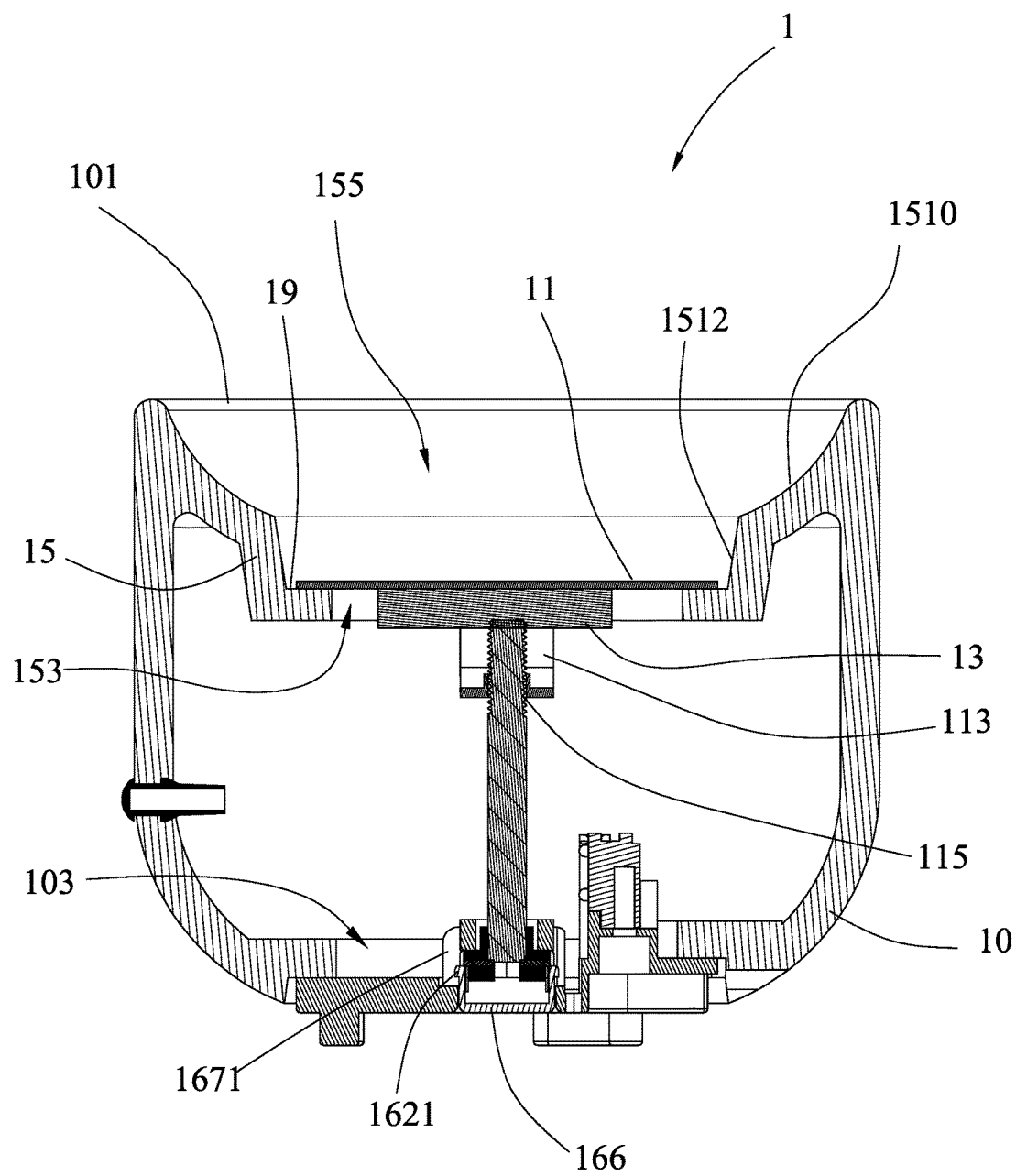
FIG. 4 is a sectional side view of the aroma diffuser having an aroma capsule in accordance with the present invention.

Referring also to FIG. 3 and FIG. 4, in this embodiment, the holder member 15 further comprises an inside flange 19 and a bottom hole 153. The inside flange 19 extends downwardly inwards from a top side of the holder member 15. The bottom hole 153 is defined in an opposing bottom side of the holder member 15 and surrounded by the inside flange 19. The heat conduction device 11 is supported on a top side of the inside flange 19. The heating element 13 is mounted in the bottom hole 153, and kept in contact with the heat conduction device 11.

Referring to FIGS. 1, 3 and 4 again, in this embodiment, the holder member 15 further comprises an upper arched wall 1510 and a lower upright wall 1512. The upper arched wall 1510 and the lower upright wall 1512 surround the holding chamber 155. The upper arched wall 1510 curves inwardly from the top side of the hollow housing 10, exhibiting a bowl-shaped configuration that is wide at the top and narrow at the bottom. The lower upright wall 1512 extends downwardly from the upper arched wall 1510 to the inside of the holder member 15. Thus, when placing the aroma capsule 12 in the holding chamber 155 of the holder member 15, the bottom surface of the aroma capsule 12 is surrounded by the lower upright wall 1512 and kept in contact with the heat conduction device 11, the opposing top surface of the aroma capsule 12 is surrounded by the upper arched wall 1510, and an arched gap 1551 is defined between the placed aroma capsule 12 and the upper arched wall 1510 for the insertion of the user's plump fingers to put the aroma capsule 12 in the holder member 15, or to take the aroma capsule 12 out of the holding chamber 155 of the holder member 15 for replacement. An equivalent holder member of a conventional aroma diffuser is an added external member that does not have the said upper arched wall. The design of the present invention allows the user to smoothly put the aroma capsule 12 in the holder member 15, or to conveniently take the aroma capsule 12 out of the holder member 15 for replacement.

In this embodiment, the holder member 15 is formed integral with the hollow housing 10 and inwardly extended from the top side of the hollow housing 10. Further, the material of the aroma diffuser 1 can be selected from the group of ceramic, metal, wood and plastics. In this embodiment, ceramic is selected for making the aroma diffuser for the advantages of electrical insulation and heat resistance characteristics and aesthetic appearance. In this embodiment, ceramic is used to make the hollow housing 10 and the holder member 15 in one piece. When compared to the conventional design in which the hollow housing and the holder member are independent members made of different materials, the invention has the hollow housing and the holder member be integrally made in one piece without further labor and time-consuming assembly steps, saving component cost and enhancing structural stability.

Figure 5:
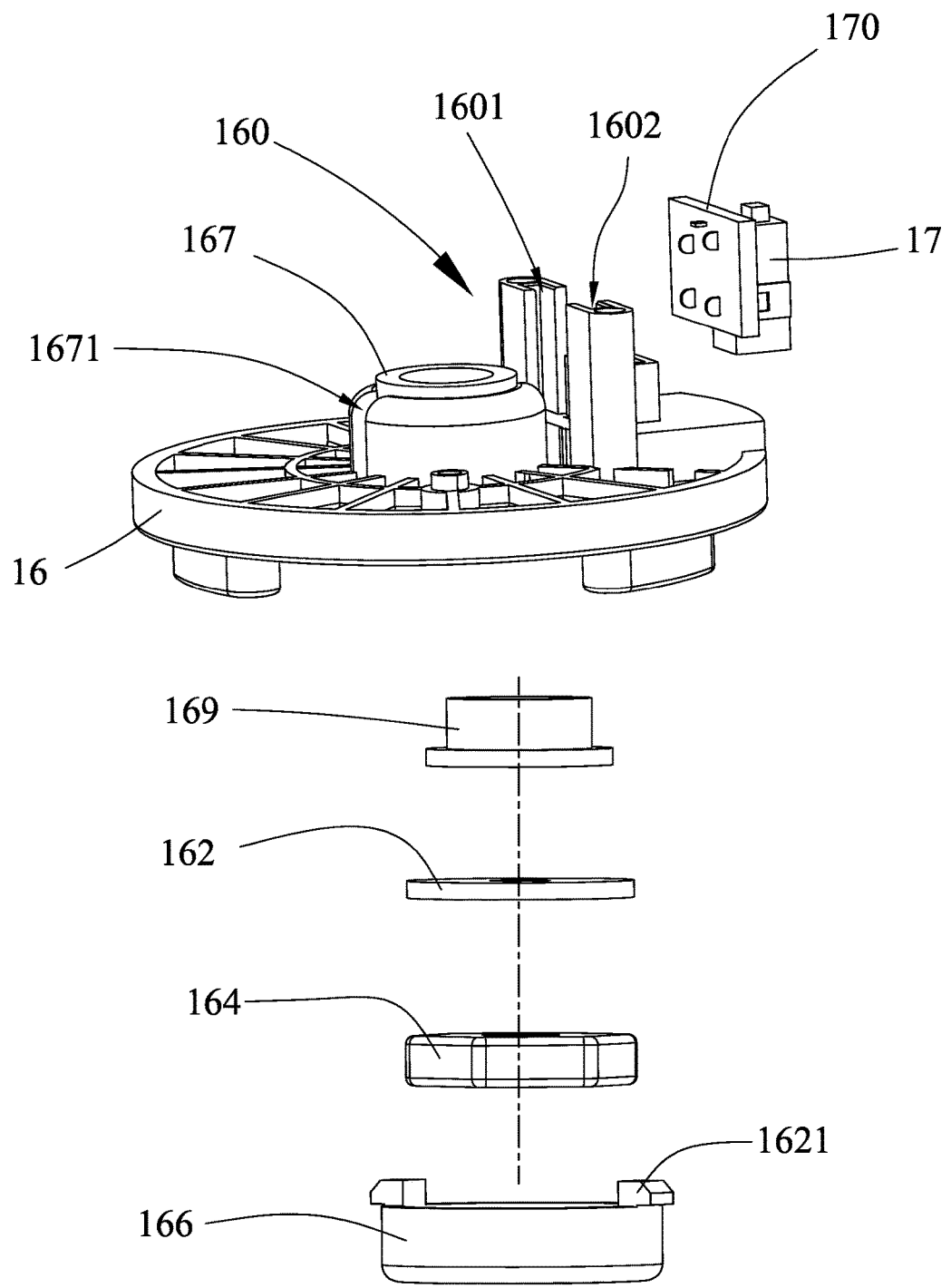
FIG. 5 is an exploded view of the bottom cover of the aroma diffuser having an aroma capsule in accordance with the present invention.

Referring to FIG. 5 and FIGS. 2 and 4 again, the heat conduction device 11 further comprises a mounting frame 113 on a bottom side thereof. The mounting frame 113 comprises a screw rod 30 and a bottom cover 16. The bottom cover 16 is fastened to the second opening 103 of the hollow housing 10. The heating element 13 is stopped against a bottom surface of the heat conduction device 11. The screw rod 30 has one end thereof fastened to the bottom cover 16, and an opposite end thereof inserted through the mounting hole 115 and tightly stopped at the bottom surface of the heating element 13 against the heat conduction device 11 to hold the heating element 13 and the heat conduction device 11 in positive contact with each other, maintaining the stability of heat conduction.

The heat conduction device 11 is made of a thermally conductive material. Preferably, the heat conduction device 11 is selected from the material group of metal, ceramic and glass. The heat conduction device 11 is configured to adapt the shape of the aroma capsule 12. The aroma capsule 12 comprises a shell made in the form of a metal film container, and an aroma, such as scented wax or essential oil contained in the shell.

Further, the heating element 13 can be a metal heating element, ceramic heating element, polymer PTC heating element or composite heating element. In the present preferred embodiment, the heating element 13 is a polymer PTC (positive temperature coefficient) heating element (PTC semiconductor heating element or PTC thermistor).

Referring to FIGS. 2, 4 and 5 again, in the present preferred embodiment, the aroma diffuser 1 further comprises a DC power socket 17 and a printed circuit board 170 (PCB). The DC power socket 17 and the printed circuit board 170 are electrically coupled together and mounted in the hollow housing 10. The printed circuit board 170 is electrically coupled with the heating element 13 to provide the heating element 13 with the necessary working power. The bottom cover 16 comprises a mount 160 located at a top side thereof. The DC power socket 17 and the printed circuit board 170 are coupled together and mounted on the mount 160. The mount 160 comprises a first retaining groove 1601 and a second retaining groove 1602. The first retaining groove 1601 and the second retaining groove 1602 are symmetrically upwardly extended from a top wall of the bottom cover 16. The printed circuit board 170 is plugged into the first retaining groove 1601 and the second retaining groove 1602.

Figure 6:
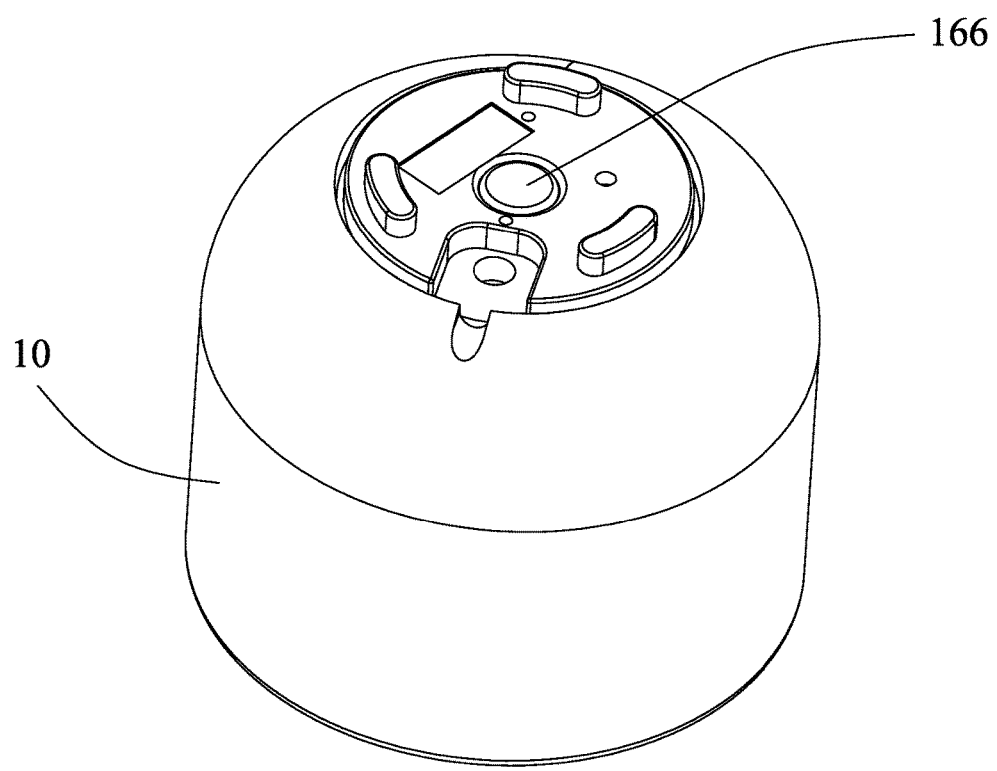
FIG. 6 is an oblique bottom elevational view of the aroma diffuser using an aroma capsule in accordance with the present invention.

Referring to FIG. 6 and FIGS. 1, 4 and 5 again, in the present preferred embodiment, the bottom cover 16 further comprises an upright barrel 167, a flanged lagging sleeve 169, a washer 162, a screw nut 164 and an anti-tamper buckle 166. The upright barrel 167 extends vertically upwardly from a center through hole (not shown) of the bottom cover 16 to a predetermined height. The screw rod 30 has its one end inserted into the upright barrel 167. The flanged lagging sleeve 169 is made from silicon rubber. In installation, insert the flanged lagging sleeve 169 upwardly into the upright barrel 167 at the center of the bottom cover 16 and sleeve the flanged lagging sleeve 169 onto the screw rod 30, and then attach the washer 162 onto the screw rod 30, and then thread the screw nut 164 onto the screw rod 30 to stop the washer 162 against the flanged lagging sleeve 169, and then fasten the anti-tamper buckle 166 to the screw nut 164. Thus, the upright barrel 167 and the flanged lagging sleeve 169 prohibit transfer of heat energy from the heating element 13 through the screw rod 30 to the DC power socket and the printed circuit board 170, avoiding electronic component damage. Further, the anti-tamper buckle 166 comprises two hooks 1621 located at a top edge thereof. The upright barrel 167 comprises two retaining grooves 1671 located on an inside wall thereof. The anti-tamper buckle 166 is attached to the periphery of the screw nut 164 to force the hooks 1621 into engagement with the respective retaining grooves 1671 of the upright barrel 167 to prevent non-professional persons or children from unwillingly dismantling the screw nut, avoiding component damage and dangers.

Referring to FIGS. 1 and 2 again, the aroma diffuser 1 has an aroma capsule 12 placed therein. The aroma capsule 12 is placed in the holder member 15. The aroma capsule 12 further comprises a disposable container 121 and an aroma 125. The disposable container 121 comprises an opening 1211 and a protruding edge 1213. The protruding edge 1213 extends outward from the opening 1211. The protruding edge 1213 allows the user to move and operate the aroma capsule 12 easily and conveniently. The aroma 125 is contained in the disposable container 121. The aroma 125 is, for example, a scented wax, essential oil, flavor block or fragrance stone. In the present preferred embodiment, the aroma 125 is a scented wax.

Referring to FIG. 1 again, in the present preferred embodiment, the aroma capsule 12 further comprises a breathing film 123 sealed to the opening 1211 of the disposable container 121 to stop the melted scented wax or aroma from flowing out of the aroma capsule, assuring safety.

Further, the disposable container 121 to be directly manipulated by the user is an aluminum foil shell, thus, there is nothing for the user to worry about breaking the disposable container 121 or washing the disposable container 121. Further, the user does not need to prepare an extra container for holding the aroma 125.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. An aroma diffuser using an aroma capsule, comprising: a hollow housing, a DC power socket and a printed circuit board electrically coupled together and mounted inside said hollow housing, a heat conduction device and a heating element, wherein said hollow housing comprises a first opening located on a top side thereof, a second opening located on an opposing bottom side thereof and an integrated holder member downwardly inwardly extended from the said top side, said holder member defining therein a holding chamber facing toward said first opening; said heat conduction device is mounted in said holding chamber; said heating element is mounted at a bottom side of said heat conduction device and kept in positive contact with said heat conduction device and electrically connectable to a power supply unit for generating heat to heat said heat conduction device; said printed circuit board is electrically coupled with said heating element to provide said heating element with the necessary working power, wherein said holder member further comprises an upper arched wall and a lower upright wall surrounding said holding chamber, said upper arched wall curving inwardly from the said top side of said hollow housing and having a wide top and a narrow bottom, said lower upright wall being extended downwardly from said upper arched wall to the inside of said holder member;

wherein said heat conduction device further comprises a mounting frame mounted at a bottom side of said heat conduction device and defining therein a mounting hole; the aroma diffuser further comprises a screw rod and a bottom cover, said bottom cover being fastened to said second opening of said hollow housing, said heating element being abutted against the said bottom side of said heat conduction device, said screw rod having one end thereof fastened to said bottom cover and an opposite end thereof inserted through said mounting hole and stopped at heating element against said heat conduction device;

wherein said bottom cover further comprises a mount mounted on a top side thereof; said DC power socket and said printed circuit board are mounted at said mount;

wherein said bottom cover further comprises an upright barrel vertically upwardly extended from a bottom edge thereof and attached onto said screw rod, a flanged lagging sleeve inserted into said upright barrel and sleeved onto said screw rod, a washer mounted on said screw rod, and a screw nut threaded onto said screw rod and stopped at said washer against said flanged lagging sleeve.

2. The aroma diffuser using an aroma capsule as claimed in claim 1, wherein said holder member further comprises an inside flange and a bottom hole, said inside flange being extended downwardly inwards from a top side of said holder member, said bottom hole being defined in an opposing bottom side of said holder member and surrounded by said inside flange; said heat conduction device is supported on a top side of said inside flange and abutted to said bottom hole; said heating element is mounted in said bottom hole and kept in contact with said heat conduction device.

3. The aroma diffuser using an aroma capsule as claimed in claim 1, wherein said upper arched wall exhibits a bowl-shaped configuration.

4. The aroma diffuser using an aroma capsule as claimed in claim 1, further comprising an aroma capsule placed in said holding chamber of said holder member, said aroma capsule having a bottom side thereof supported on said lower upright wall and kept in contact with said heat conduction device and an opposing top side thereof suspended in said upper arched wall and defining with said upper arched wall an arched gap therebetween.

5. An aroma diffuser using an aroma capsule, comprising: a hollow housing, an anti-tamper buckle, a heat conduction device and a heating element, wherein said hollow housing comprises a first opening located on a top side thereof, a second opening located on an opposing bottom side thereof and an integrated holder member downwardly inwardly extended from the said top side, said holder member defining therein a holding chamber facing toward said first opening; said heat conduction device is mounted in said holding chamber; said heating element is mounted at a bottom side of said heat conduction device and kept in positive contact with said heat conduction device and electrically connectable to a power supply unit for generating heat to heat said heat conduction device; said anti-tamper buckle comprises a plurality of hooks hooked in said upright anti-tamper buckle, wherein said upright barrel comprises a plurality of retaining grooves respectively forced into engagement with said hooks of said anti-tamper buckle, wherein said holder member further comprises an upper arched wall and a lower upright wall surrounding said holding chamber, said upper arched wall curving inwardly from the said top side of said hollow housing and having a wide top and a narrow bottom, said lower upright wall being extended downwardly from said upper arched wall to the inside of said holder member;

wherein said heat conduction device further comprises a mounting frame mounted at a bottom side of said heat conduction device and defining therein a mounting hole; the aroma diffuser further comprises a screw rod and a bottom cover, said bottom cover being fastened to said second opening of said hollow housing, said heating element being abutted against the said bottom side of said heat conduction device, said screw rod having one end thereof fastened to said bottom cover and an opposite end thereof inserted through said mounting hole and stopped at heating element against said heat conduction device.

6. The aroma diffuser using an aroma capsule as claimed in claim 5, wherein said holder member further comprises an inside flange and a bottom hole, said inside flange being extended downwardly inwards from a top side of said holder member, said bottom hole being defined in an opposing bottom side of said holder member and surrounded by said inside flange; said heat conduction device is supported on a top side of said inside flange and abutted to said bottom hole; said heating element is mounted in said bottom hole and kept in contact with said heat conduction device.

7. The aroma diffuser using an aroma capsule as claimed in claim 5, wherein said upper arched wall exhibits a bowl-shaped configuration.

8. The aroma diffuser using an aroma capsule as claimed in claim 5, further comprising an aroma capsule placed in said holding chamber of said holder member, said aroma capsule having a bottom side thereof supported on said lower upright wall and kept in contact with said heat conduction device and an opposing top side thereof suspended in said upper arched wall and defining with said upper arched wall an arched gap therebetween.

9. The aroma diffuser using an aroma capsule as claimed in claim 5, further comprising a DC power socket and a printed circuit board electrically coupled together and mounted inside said hollow housing, said printed circuit board being electrically coupled with said heating element to provide said heating element with the necessary working power.

10. The aroma diffuser using an aroma capsule as claimed in claim 9, wherein said bottom cover further comprises a mount mounted on a top side thereof; said DC power socket and said printed circuit board are mounted at said mount.

11. The aroma diffuser using an aroma capsule as claimed in claim 10, wherein said bottom cover further comprises an upright barrel vertically upwardly extended from a bottom edge thereof and attached onto said screw rod, a flanged lagging sleeve inserted into said upright barrel and sleeved onto said screw rod, a washer mounted on said screw rod, and a screw nut threaded onto said screw rod and stopped at said washer against said flanged lagging sleeve.

* * * * *